United States Patent [19]

Hessemer, Jr. et al.

[11] 4,416,552

[45] Nov. 22, 1983

[54] CORRELATION THERMOGRAPHY

[75] Inventors: Robert A. Hessemer, Jr., 757 Corpino De Pecho, Green Valley, Ariz. 85614; Lloyd J. Perper, 3725 Ironwood Hill Dr., Tucson, Ariz. 85745

[73] Assignees: Robert A. Hessemer, Jr., Green Valley; Lloyd J. Perper; Theodore Bowen, both of Tucson, all of Ariz.

[21] Appl. No.: 311,632

[22] Filed: Oct. 15, 1981

[51] Int. Cl.³ ............................................. G01K 1/00
[52] U.S. Cl. .................................. 374/117; 374/122; 128/736
[58] Field of Search ............... 374/110, 115, 163, 166, 374/117, 185, 121, 122, 101; 128/736, 664

[56] References Cited

U.S. PATENT DOCUMENTS 3,985,024 10/1976 Horak .................................... 73/587
4,235,107 11/1980 Lüdeke et al. ....................... 374/122
4,246,784 1/1981 Bowen ................................. 374/117

OTHER PUBLICATIONS

Leroy, "Microwave Radiometry and Thermography Present and Prospect".
A. Mamouni et al., "New Correlation Radiometer for Microwave Thermography", *Electronics Letters*, vol. 17, No. 16, Aug. 6, 1981, pp. 554-555.
D. A. Christensen, "Current Techniques for Noninvasive Thermography", published in Physical Aspects of Hyperthermia-G. H. Nussbaum.
*Using Microwave Techniques for High Temperature Measurement*, vol. 45, No. 2, Feb. 1972, R. Billeter from Instruments and Control Systems, pp. 107-109.
*Subcutaneous Temperatures*, vol. 190, No. 4215, pp. 669-672, Nov. 14, 1975, Grundy et al., from Science.

*Primary Examiner*—Charles E. Frankfort
*Assistant Examiner*—David R. Schuster
*Attorney, Agent, or Firm*—C. Lamont Whitham

[57] ABSTRACT

Correlation thermography permits high resolution passive remote thermal radiation sensing for non-invasive temperature measurement of the interior of a body. At least two directional transducers are coupled to the surface of the body at different locations about the body in such a manner that their directional receiving patterns intersect. These transducers may be acoustic or electromagnetic transducers, but in any case are capable of receiving thermally-generated energy from inside the body and generating corresponding electrical signals. The intersection of the receiving patterns of the transducers defines a common volume which is relatively small, and the signals at each transducer originating from this common volume within the body exhibit a high degree of correlation. A multiplier receives the electrical signals produced by the transducers. A fixed or variable delay is interposed between at least one of the transducers and the multiplier. A low pass filter or integrator is connected to average the product output signal from the multiplier and thereby generate a correlation output signal which is a measure of the thermally-generated energy within the common volume of intersection of the directional receiving patterns of the transducers.

20 Claims, 20 Drawing Figures

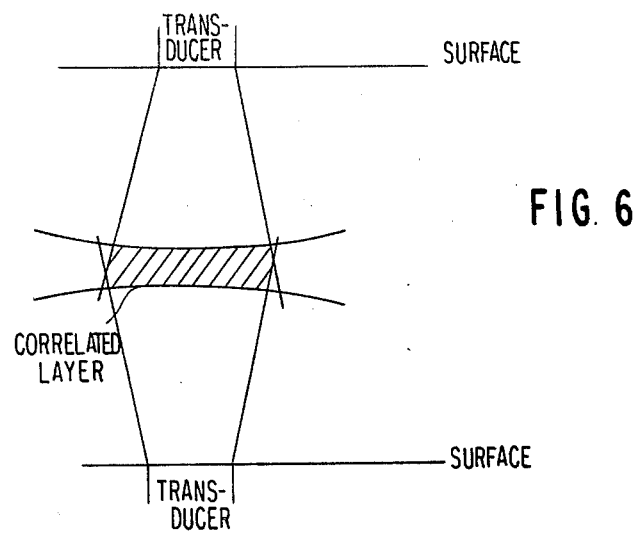
FIG. 6
FIG. 7
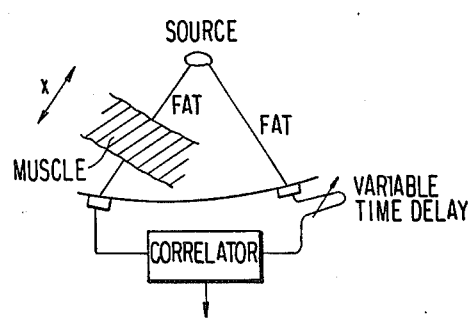
FIG. 9
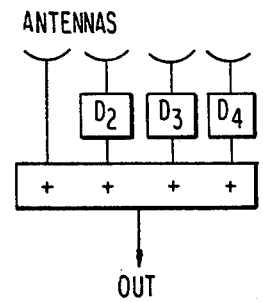
FIG. 10
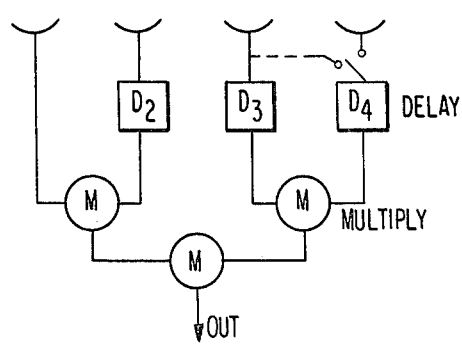
FIG. 11
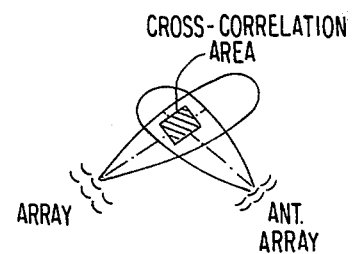

NARROW WIDE
BAND BAND

CORRELATION THERMOGRAPHY

BACKGROUND OF THE INVENTION

The subject invention generally relates to the measurement of temperatures within a body, and more particularly to a system of temperature measurement by monitoring the correlations in thermally-generated energy from inside the body.

There are many situations in medical diagnosis and treatment, industrial processing, geophysical exploration, and other fields where it is desirable to measure the temperature inside a material body, but it is not practical to insert a probe beyond the surface of the body. In medical diagnosis, the usefulness of temperature measurement at the few places available for probe insertion is well established. In recent years, thermograms produced by infrared camera equipment and other surface temperature measurement have shown promise as a means of detecting breast cancer lesions. A technique which extends temperature measurement to all soft-tissue parts of the body would be a powerful new diagnostic tool.

In medical therapy, a non-invasive temperature monitoring technique would be useful in almost any procedure involving heating or cooling of the soft tissues of the body. For example, hyperthermia has been found to be a promising technique, either alone or in combination with other modalities, for the treatment of cancer. However, its effectiveness is very sensitive to the temperature which is reached, becoming more effective as one approaches 45° C., but tissue necrosis becomes a serious problem if the temperature goes above 45° C. Therefore, a non-invasive method of monitoring temperature profiles is important if hyperthermia is to have wider potential.

In industrial processing, a suitable temperature distribution inside a large, hot body is often important during the heat treatment and cooling process. For example, the casting of large thickness of glass and other brittle materials is costly, partly because of a high failure rate which might be alleviated by a non-invasive temperature monitoring system. Data needed for geophysical exploration and monitoring would be more readily obtained if non-invasive techniques could provide temperature profiles as a function of depth for distances of several meters into surface rocks or into the region around a bore hole.

One technique for non-invasive measurement of temperature is electromagnetic radiometry which is based on so-called black body radiation. This is electromagnetic energy inherently radiated by bodies having temperatures above 0° K. Infrared frequencies have been detected to provide thermograms of the surfaces of bodies. In order to detect thermally generated energy below the surface of a body, longer wavelength microwave frequencies are detected. Another technique for non-invasive measurement of temperature is described in U.S. Pat. No. 4,246,784 to Theodore Bowen. This technique may be described as acoustic radiometry. While both of these techniques are useful for making non-invasive temperature measurements, what is actually measured in either case is an average temperature along the axis of the directivity pattern of the transducer or antenna used to receive the thermally-generated energy.

SUMMARY OF THE INVENTION

It is, therefore, an object of this invention to make a non-invasive temperature measurement of defined volumes within a body from thermal noise correlations.

It is another object of the invention to provide a passive remote temperature sensor system for non-invasive temperature profile measurement of the interior of a body.

It is a further object of the present invention to provide a method of passive, non-invasive temperature measurement of the interior of a body using the thermal noise spectra radiated from within the body and correlated in two or more receivers.

The foregoing and other objects of the invention are accomplished by receiving the thermal noise spectra along two well-defined paths within the interior of the body. This is conveniently done by coupling two antennas or transducers with the surface of the body to intercept the thermally-generated energy from a common volume within the interior of the body along said paths. The antennas or transducers convert the received thermal noise into corresponding electrical signals. These signals are multiplied together and then integrated giving an output that is proportional to the common volume temperature within a body.

Correlation receivers are used in radio astronomy but for a different purpose than in our non-invasive temperature technique. Kraus (Radio Astronomy, pp. 255–258) lists several advantages of correlation receivers relative to the classic Dicke receiver. For one thing it is more sensitive by a factor of $2\sqrt{2}$. Also the correlation receiver does not have a switch with its additional losses. In addition, the correlation technique can be used with one antenna under certain conditions. Basically in radio astronomy, correlation is used to increase the receiver sensitivity.

In non-invasive temperature measurement, correlation is used for quite a different reason. Single antenna non-invasive temperature techniques with a Dicke receiver now are able to measure temperature inside a body. However, with a single antenna all the weighted effects of 'hot' objects that are in the antenna pattern at various depths are measured. This means that several 'hot' spots at different depths are averaged together to give a single temperature. Without further measurements the depth of the object or objects is not known.

With two antennas spaced apart at the surface with patterns that intersect to give a small common volume at the desired depth, correlation allows for the measurement of only the temperature within this intersection volume of the two antennas. Hot spots that lie in only one of the antenna patterns are effectively made transparent by the correlation process.

In radio astronomy the two antennas are separated on the ground a distance that is infinitesimal compared with the distance to the galaxies. Thus the two antenna patterns have a common volume that starts not too many miles away from earth. This means that they do not use correlation to measure temperature at a controllable depth. In our non-invasive temperature measurement, correlation is used to measure temperature at a controllable depth and in a small finite volume.

Current research projects reported in the literature using E-M or acoustical radiation to measure temperature non-invasively use only a single antenna or transducer. They cannot measure temperature at a known depth with a single measurement. Our correlation technique overcomes this limitation.

BRIEF DESCRIPTION OF THE DRAWINGS

The foregoing and other objects, aspects and advantages of the invention will be better understood from the following detailed description of the invention with reference to the accompanying drawings, in which:

FIGS. 4, 5 and 6 illustrate various geometries for the placement of the transducers;

FIG. 7 is a diagram used to illustrate the suitability of the human body as a propagation medium for microwave thermography;

FIGS. 9 and 10 are diagrams of summation and multiplication configurations respectively, for a system employing more than two antennas;

FIG. 11 is a diagram of a system using arrays of antennas;

DETAILED DESCRIPTION OF THE INVENTION

Figure 1:
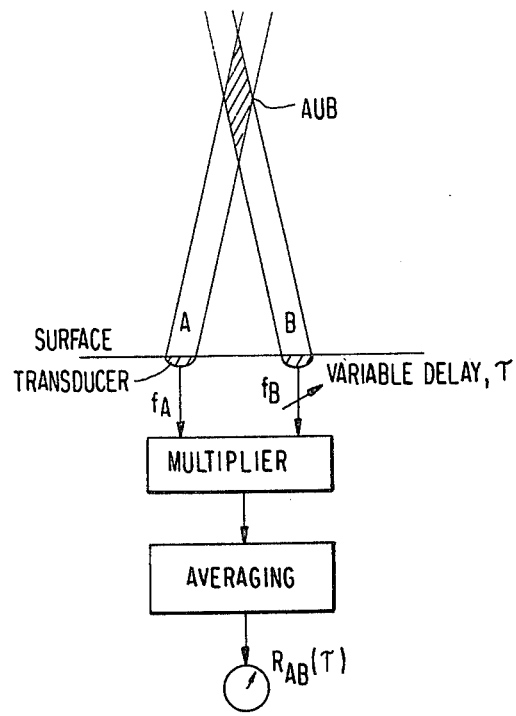
FIG. 1 is a diagram illustrating the basic arrangement for correlation thermography according to the invention.

Acoustic-radiometric temperature sensing is based upon an analogy between electro-magnetic and acoustic (i.e., elastic wave) radiation. It should be understood, however, that electro-magnetic and acoustic waves are entirely different physical phenomena, one being a phenomenon of electric and magnetic fields propagating in empty space, the other being a property of the mechanical motions of material media (solids, liquids, gases). There are many similarities in the mathematics of electro-magnetic and acoustic waves which result in some analogies of behavior.

In the case of electro-magnetic radiation, it is well-known that any surface at any absolute temperature $T>0$ emits "black-body" radiation. A broad band of frequencies is emitted from 0 to an upper limit determined by the temperature T. For example, for objects at temperatures in the neighborhood of room temperature, the frequencies extend through radio and microwave frequencies into infrared frequencies. Many temperature measuring systems determine temperature of the surface of a "black-body" by measuring the intensity of all or some portion of the "black-body" spectrum. For example, pyrometers make use of the visible "black-body" radiation, comparing the apparent color of the radiation from the surface of unknown temperature to that of a surface of known temperature. Infrared cameras measure surface temperature by the intensity of infrared emissions. Less well-known are microwave radiometers, which determine temperature by measuring the intensity of "black-body" radiation in the microwave frequency region. When only the microwave frequencies are measured, the total intensity is directly proportional to the absolute temperature T of the "black-body" surface. It is possible to measure temperatures down to within a few degrees from absolute zero with a microwave radiometer. In fact, the most publicized application of this technique has been the measurement of "cosmic" or extraterrestrial 3° K. "black-body" radiation which is attributed to the remnants of the "big bang" in cosmological theory.

Microwave thermography has been under study as a potentially useful means for detecting certain cancers (viz. breast), both alone and in combination with auxiliary information. In that technique, microwave frequency components of thermal radiation from tumorous regions are compared with those from their surroundings, and small differences (order of 0.1° C. resolution) are observed. The thermal anomalies associated with some cancers have been detected as much as several centimeters below the surface, but with coarse resolution (centimeters) of the observed volume as compared with local point measurements (viz. by implanted thermistors).

The current microwave thermographic art derives largely from the experience of radio astronomy, out of which the Dicke-switched, low-noise radiometer has been applied. In that type of device, the receiver input is switched at a slow rate (viz. 8 Hz.) between the receiving antenna and a matched load (both are held at reference temperatures); the receiver output is square-law detected, and the envelope is synchronously detected relative to the switching signal.

System noise, including the significant portion arising from the receiver input stage, which originates after the Dicke switch, does not have a coherent envelope, and is suppressed in the synchronous detector and its output averaging circuitry. The thermal energy components entering the antenna within the band-pass are switched, and their envelope is synchronously detected, permitting the resolution of small fractions of a degree in the presence of hundreds of degrees of system temperature.

In current microwave thermography, a matched antenna at the surface of the skin is connected to a radiometer, whose output is typically measured at several positions and in one or two frequency bands. At frequencies on the order of 1 Ghz., the $e^{-1}$ penetration depth ranges from 2 to 10 cm. (decreasing with water content), whereas at 5 Ghz. it ranges from about 0.5 to 3 cm.; typical resolutions in position at the two frequencies might be 10 cm. and 2 cm. respectively.

The user is faced with a trade-off between penetration depth and resolving power; whereas it would be desirable to be able to resolve 2 cm. at a depth of 10 cm., the technique will provide the resolution or the depth, but not both at the same time. Moreover the attenuation of microwave energy with depth tends to weight the observed radiating sources toward the surface, so that the effects of deep sources are reduced and can be masked by smaller variations near the surface. What is needed at depth is a technique that inherently discriminates against shallow sources. The method of this invention is based on spatial correlation.

Acoustical passive systems to detect interior temperatures are described in the aforementioned U.S. Pat. No. 4,246,784 to Bowen. This patent describes systems for sensing temperature using a single transducer analogous to the Dicke-switched, low-noise radiometer now in use at microwave frequencies. The extension of detecting acoustical noise to a two transducer, correlation type receiver is related to microwave correlation temperature sensing. One major difference between an acoustical correlation temperature detector versus one at microwave frequencies is in the wavelengths for measurement of temperature inside a human. These data are given later and show the acoustical wavelength to be some 20 or more times smaller. The unique capabilities of an acoustic radiometer temperature sensing system result from the acoustical attenuation verses frequency characteristics of a wide variety of materials, and from the short wave lengths of the acoustic radiation in the useful range of frequencies. For all materials, the attenuation is small at low frequencies, and increases with frequency; thus, any desired amount of attenuation can be selected by choosing the appropriate frequency. Many liquids exhibit "classical" absorption which is proportional to frequency squared. Over limited ranges of frequencies, many materials have an acoustic attenuation directly proportional to the frequency. This is true, for example, for most polycrystalline metals and for most soft tissues of the human body. One convenient way to characterize attenuation is to specify the distance in which the wave amplitude is attenuated by some specified fraction (usually 1/e). Since the intensity is proportional to the amplitude squared, the intensity would be reduced by $1/e^2$ in one attenuation length.

Consider the specific example of medical applications of acoustical thermography. It is well-established that attenuation of ultrasound in body tissue is proportional to frequency, so that one can write the contribution of thermal noise power by the layer between x and dx as $kbf \cdot T(x) \exp(-bfx)dx$, where k is the Boltzmann constant, b is a constant characteristic of tissue (a typical value for soft tissue is $b = 0.2(cm-MHz)^{-1}$), f is the frequency, and T(x) is the temperature at depth x. From this expression, one can show that this layer makes its maximum contribution to the received noise power at a frequency $f(max) = 1/(bx)$. At a lesser depth, the maximum is located at a higher frequency.

Suppose the temperature distribution is desired at a depth of 16 cm. in soft tissue. Then the frequency f approximately equals $1/(0.2)(16) = 0.3$ MHz. Since the wavelength $\lambda = c/f$, where c is the velocity of sound ($c \approx 0.15$ cm/sec. in soft tissue), $\lambda \approx 0.5$ cm. This is very convenient since any device to create a directional beam sensitivity pattern must have dimensions large compared to a wavelength. This being the case, a diameter $d \approx 5$ cm. of the acoustic transducer might be conveniently selected. The frequencies involved are also conveniently high so that the measurement time is not too long.

For materials in which attenuation is proportional to frequency, the attenuation length is a fixed multiple of the wavelength. For example, using the numbers given above for tissue, this ratio $R = 67$. In many materials of geophysical interest, $R \approx 100$ to 500. It can be seen from the manner in which R was calculated that it corresponds to the number of cycles of oscillation for the wave motion to decrease to 1/e of its original amplitude. Whatever the value of R, if large attenuation lengths are desired in order to sense temperature to great depth, one must utilize frequencies which correspond to long wavelengths ($\lambda \approx$ (depth of interest)/R). Since $f = c/\lambda$, where c is the acoustic or elastic wave velocity in the medium of interest, this means going to low frequencies. At least two difficulties may arise:

(1) The time required to obtain a given temperature precision will increase as $1/\Delta f$.

(2) The noise background from other sources (wind, surf, seismic activity, human activity) may increase.

Referring now to FIG. 1 of the drawings, suppose that two transducer beams, A and B, receive thermally-generated acoustical energy from inside the body, and that the transducer outputs (amplified and possibly shifted to a common intermediate frequency) are multiplied and smoothed (rather than added, as would correspond to a phased array). Then the processor output would consist of the cross-correlation function of the contents of the two channels.

In the oversimplified context of FIG. 1, noise components received in beam A alone, or B alone, multiply incoherently with noise in the other beam, and are reduced in magnitude at the output of the cross-correlation process. In the intersection region, each component is received in both channels, subject to variations in amplitude and relative delay, depending on the position of the component source and the structure of the propagation medium, so that correlation exists and output $R_{AB}(\tau)$ occurs.

For noise components whose sources are symmetrically located with respect to the beams, the two received components, $f_A$ and $f_B$, from the beams will tend to be identical, so that the output of the processor extracts their autocorrelation function. Other components from the beam intersection region will have distributed amplitudes and delays, but will tend to autocorrelate as a result of having the same shape. If the correlation time is long compared with the beam transit time difference (as would be the case in the absence of wide receiver bandwidths), all the components in the beam intersection tend to autocorrelate over a range of values of variable delay, which is then not very useful as a discriminant in resolving a limited part of the region.

Figure 2:
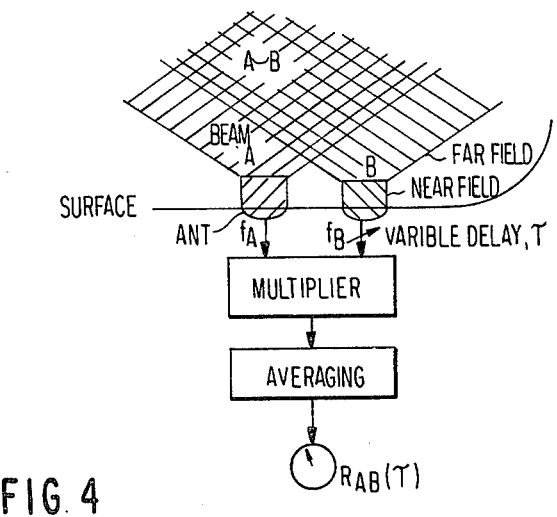
FIG. 2 is a diagram similar to FIG. 1 wherein the transducers are microwave antennas.
Figure 3:
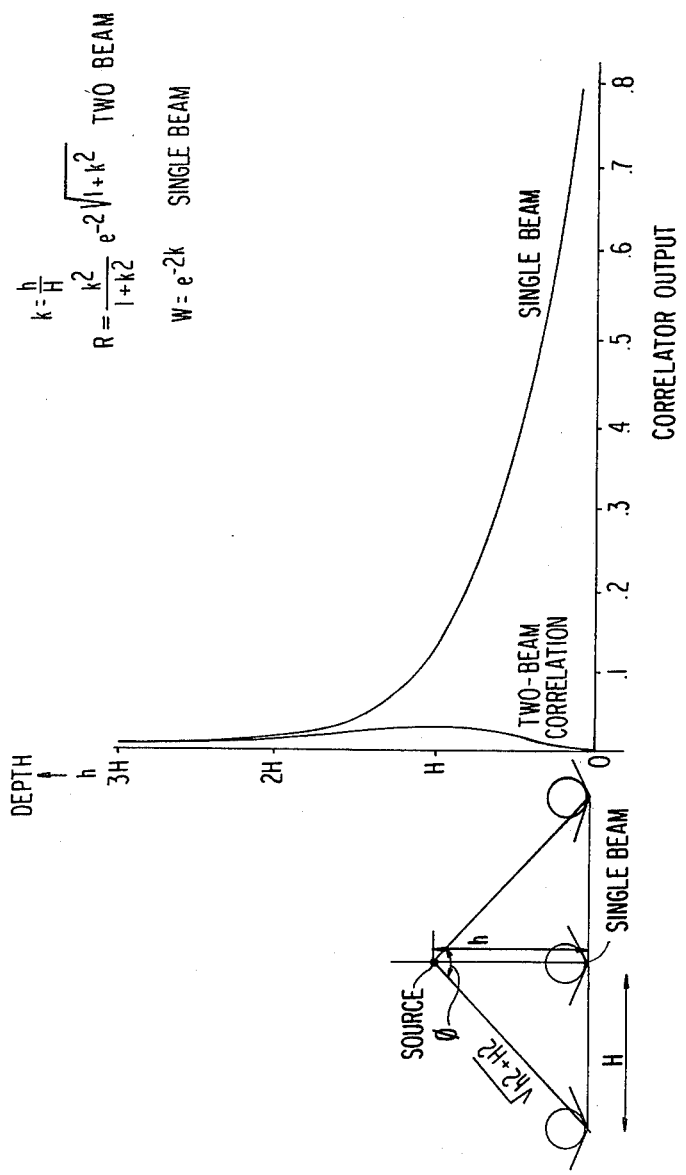
FIG. 3 is a graphical illustration of the difference between single beam and two-beam correlation.

The discriminants that determine resolution in FIG. 1 are the beam patterns and the characteristics of the illuminated regions of the propagation medium. The case of microwave correlation thermography is illustrated in FIG. 2. The far-field beam widths shown are arbitrarily bounded (viz. by the $-6$ dB angles of a dipole), whereas angular coverage is actually continuous (preferably with nulls along or near the surface). Near the surface, resolution is facilitated by the suppression of correlated components in the output as a result of beam directivity, contingent on its preservation at low angles in the propagation medium. At depth, resolution tends to be determined by propagation, which is inhomogeneous as a result of the internal body structure. Nevertheless the oversimplification of a homogeneous medium offers some insight into the comparison of cross-correlation radiometry vs. single beam radiometry. In FIG. 3, the processed outputs are compared for a component source whose position is varied along the line of symmetry. Sine-function antenna patterns are applied; in the former case, the geometry of FIG. 2 is used; in the latter a single antenna at the base of, and directed along, the line of symmetry is assumed. In both cases, exponential attenuation is assumed, with $e^{-1}$ ratio in a distance, H. The curves show that two-beam correlation tends to give results comparable with single beam output for sources at depth, while strongly distinguishing against shallow sources. Since the penetration depth actually varies along the propagation paths, it is necessary to model the internal body structure to approximate the real situation for any location; however, the basic tendency of FIG. 3 would always be present.

Figure 4:
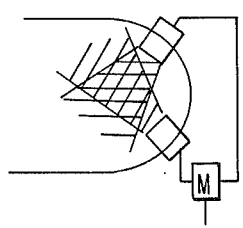
Figure 5:
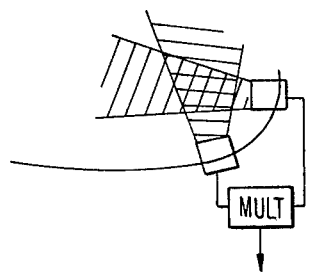

Other geometries as shown for example in FIGS. 4 and 5 are alternatively possible, including narrower beams with centerlines intersecting at various arbitrary angles. While the geometrics shown in FIGS. 1 and 2 are of near parallel beams intersecting at small angles, this type of geometry tends to give correlation over an elongated region along the beams. An alternative to even the larger angle intersections shown in FIGS. 4 and 5 is the case of beam intersection angles in the vicinity of 180° as illustrated in FIG. 6. For this condition, the spatial correlation resolution pattern is orthogonal to the beams, permitting the resolution of slices as fine as one millimeter thick in the acoustical case.

Time is also a possible discriminant. If the bandwidth of reception could be made sufficiently wide, and the conditions of measurement were compatible, it is conceivable that the cross-correlation output could show significant narrowing of the resolved volume. In such a case, the observed volume could be scanned by varying the cross-correlation time delay. For instance, suppose that two receivers having identical response 1 GHz wide in the microwave application or 1 MHz in the acoustical application were used. Their correlation function output for a common input would be the Fourier transform of the power spectrum (in this case, the constant approximating the noise spectrum, multiplied by the square of the receiver amplitude response spectrum); its width would typically be 2 nanoseconds (microwave) or about 2 microseconds (acoustical), depending on the shape of the receiver response. A variable delay in one of the receiver inputs corresponding to a range of 60 cm in free space (microwave) or 0.3 cm. in soft tissue (acoustical) would then trace out a pulse having the shape of the auto-correlation function of the system if a discrete thermal source were scanned; in the case of a thermal anomaly between two antennas in a dielectric region where the wavelength is halved, the delay would correspond to the order of 15 cm. in distance, and by scanning in delay, the peak of the function could be located more accurately. In regions containing larger amounts of moisture, the 15 cm. distance resolution could become as small as 5 cm. or less.

Correlation thermography, as a method for remote thermal sensing of deep cancers, is of special interest insofar as its added capabilities can be shown to be practically usable:
 (1) It provides a means for observing the radiation from beam intersections, to the exclusion of other energy that appears as clutter in the present art.
 (2) It may prove capable of resolving significantly in time as well as angle, depending on the practicability of measuring in very large bandwidths.
 (3) It may permit signal-to-noise ratio improvements to the extent that correlation uses information more effectively than does postdetection comparison.
 (4) It may alternatively permit shorter measuring times.

The thermal resolutions of various types of receiving systems usable in radio astronomy are known in the art. The general expression is of the form:

$$\Delta T_{min} = K_s \frac{T_{sys}}{\sqrt{\Delta \nu \cdot t}}$$

where $T_{sys}$ = system temp.
$\Delta \nu$ = bandwidth at high freq.
$t$ = low-freq. output integration time For the Dicke receiver, using square-wave modulation: $K_s = 2$.

For the correlation receiver: $K_s = (2)^{-\frac{1}{2}}$. For the same sensitivity and receiver bandwidth, the required integration time in the correlation receiver is scaled down by the factor, $$\frac{1}{(2\sqrt{2})^2} = \frac{1}{8}.$$

For $10^8$ Hz bandwidth, $10^3$ deg. K. system temperature, and 0.1 deg. C. temperature resolution for the microwave application or for $10^6$ Hz. bandwidth, 500 deg. K. system temperature, and 0.5 deg. C. temperature resolution for the acoustical application, the Dicke integration time would be 4 seconds, and the corresponding time for the correlation receiver system would be 0.5 second.

With short measurement times, the possibility exists of generating a detailed picture rather than a small grouping of points. With extended measurement time, the opportunity for more accurate thermal measurements exists. Both cases represent potentially valuable new capabilities.

In the derivation of the performance of correlation reception, the assumption was implicit that the received signals in the correlated channels would track in phase within the bandwidth. This condition would occur for identical paths, but for divergent paths of unequal length and external delay compensation, it is necessary to assure that the relative phase shift stays substantially within about $\pi/4$ radian.

Figure 8:
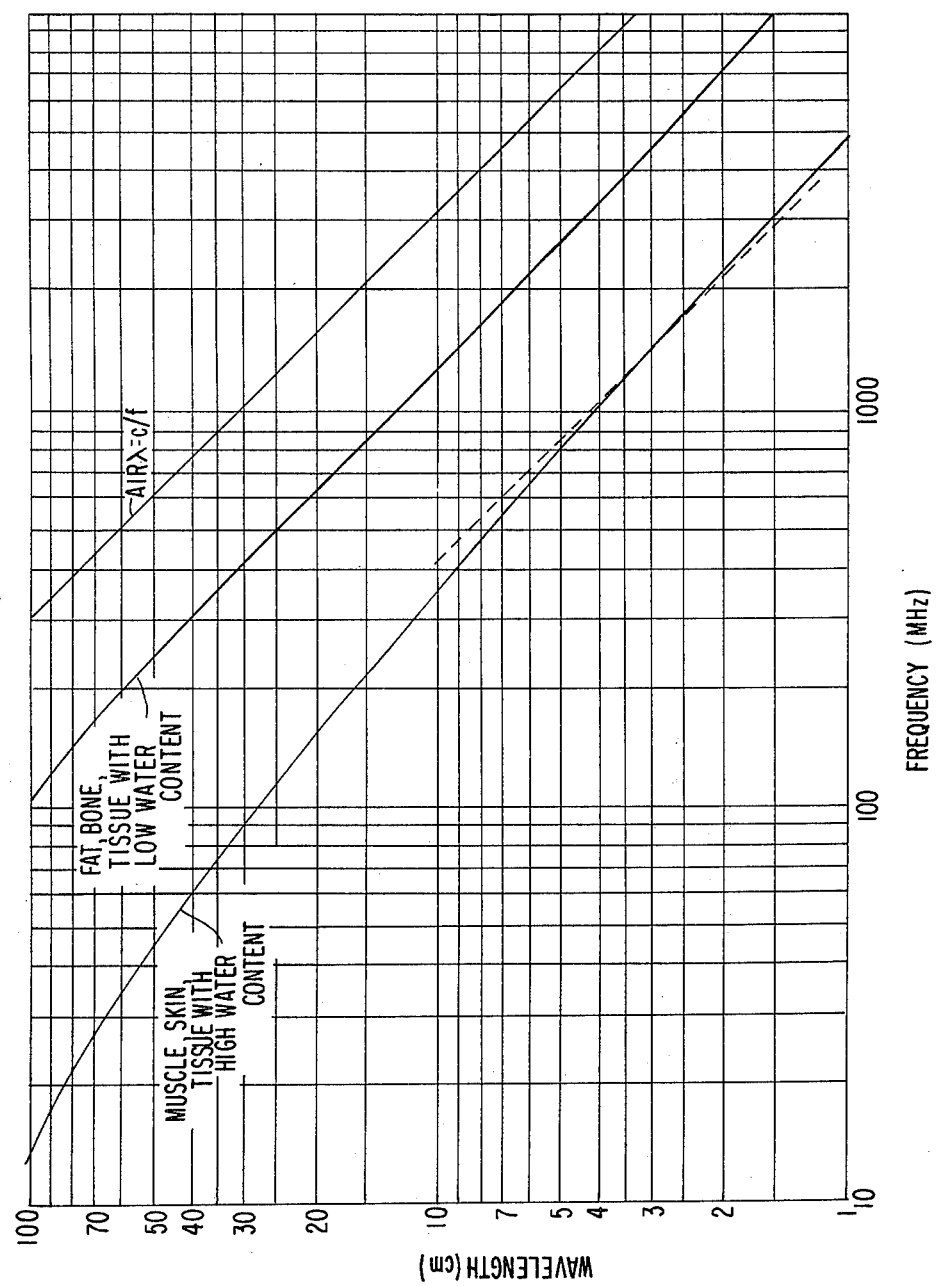
FIG. 8 is a log-log scale graph of the wavelength of microwave energy in high-dielectric regions of the body as a function of frequency.

The potential suitability of the human body as a propagation medium for broadband correlation microwave thermography may be considered in a preliminary way using a simplified model shown in FIG. 7. Suppose that microwave energy from a single region arrives at two sensing antennas via separate paths differing by the presence in one path of a high-dielectric (muscle) layer of thickness, x. Suppose that a variable time delay is inserted in the other path, and adjusted so as to maximize correlation at a frequency inside the receiver passband. The question arises of whether the energy in the channels corresponding to the two paths will correlate adequately over the total band in the presence of dispersion in the dielectric layer. The wavelength of microwave energy in high-dielectric regions of the body as a function of frequency is given in C. C. Johnson and A. W. Guy, "Nonionizing Electromagnetic Wave Effects in Biological Materials and Systems", Proc. IEEE, v. 60, no. 6, June 1972, pp. 692-713, (Table I, p. 694). The data are plotted using a log-log scale in FIG. 8. Dispersion may be seen in that the curve for muscle bends, and departs from a line parallel to the line for propagation in air. Corresponding data for fat and other material of relatively low dielectric constant are also shown.

In an ideal, dissipationless dielectric of constant, E:

$$\lambda = \frac{1}{f} \frac{c}{\sqrt{E}}$$

log λ = log c − log f − ½ log E In a dispersive region of the body, $$\lambda = \frac{1}{f} k(f),$$

where k(f) is a function of frequency. If the dispersive phase delay in the dielectric, $$2\pi \frac{x}{\lambda_H},$$

is compensated at a selected frequency, $f_1$, by the non-dispersive delay, $$2\pi f \frac{x}{k_1},$$

where $k_1 = \lambda_1 \cdot f_1$, the net differential phase delay at frequency, f, for which the wavelength in the dielectric is $\lambda_H$, is given by:

$$\Delta\phi = 2\pi \frac{x}{\lambda_H} \left(1 - \frac{f\lambda_H}{f_1\lambda_1}\right).$$

Using the data of Johnson and Guy in the foregoing expression, and assuming a muscle layer thickness of 2.81 cm. (one wavelength at 1.5 GHz. = $f_1$), the following differential phase delays are obtained for the tabulated frequencies of 0.915, 1.5, 2.45, and 5 GHz:

| f | $\lambda_H$ | radians | degrees |
|---|---|---|---|
| .915 | 4.46 | −0.12 | −7.2 |
| 1.5 | 2.31 | 0 | 0 |
| 2.45 | 1.76 | 0.23 | 13.2 |
| 5 | 0.89 | 1.106 | 63.4 |

Based on a correlation criterion of π/4 radian, bandwidths of as much as two GHz. would not be ruled out; and wider bandwidths might be feasible using a dispersive variable delay line having fixed, or adaptive characteristics.

The foregoing considerations apply to a forward wave. A more complete consideration would include the effects of reflected waves at the interfaces. For some geometries ducting effects may be anticipated in which different steady-state group and phase velocities exist, with complex effects on correlation. Polarization effects may also be expected. A plane wave incident on a tilted dissipative dielectric layer tends to generate elliptical polarization.

The problem of designing microwave antennas to operate over an octave or more in frequency may prove to be more limiting than that of dispersion. The usability of wide-band (viz. log-periodic, discone, etc.) antennas at lower frequencies gives some reason for anticipating feasible solutions, although the correlation process makes it necessary to consider additional factors such as the potential displacement of antenna phase-center as a function of frequency.

Assuming that the propagation medium, as used, permits the required order of correlation, the apparatus must have comparable constraints:

(1) The antennas should have broad frequency-independence, and be reasonably matched (VSWR 3:1) to the body over the pass-band. Helical antennas in a dielectric interface could be used.

(2) The amplifiers should have the same wide bandpass, and track in phase within about π/8 radians. Low noise (less than 5 db. noise figure) is desirable.

(3) The multiplier should have the same wide bandpass, with phase stability, and substantial isolation (20 db. or more, to suppress detection of energy in either channel alone).

(4) The variable delay should have the full band-pass, and a range of about ±1 nanosecond continuously or in steps, with low attenuation (order of 0.1 db. or less).

The correlation radiometry method according to the invention may be modified according to the following implementations:

(1) Adaptive phasing of multiple antenna elements, to give increased resolution and available received power.

(2) Reciprocal use of the phased geometry to transmit energy to thermally-identified regions.

(3) Semi-active applications, in which changes as a result of active measures are detected passively.

(4) Collateral measures such as the imposition of polarizing fields, or ionizing radiation.

The first of the above depends on the ability to correlate the energy from a specific source volume at a number of reception points, using practical hardware. The second depends on substantial validity of the reciprocity principle in a non-linear medium (for instance if use is made of a sharp threshold of linear operation as a function of power density). The third depends on the ability to modify and measure the thermal environment on a time-shared basis. The fourth depends on the ability to modify polarization selectively through bi-refringence or Faraday rotation.

Two types of combinatorial logic are of potential interest: summation and multiplication. Summation (in the appropriate phase relationships) is the appropriate means for beam formation in reception, and the necessary means for concentrating energy in transmission. Multiplication is the appropriate means for determining the antenna phases that will focus in a given region.

The configuration for summation shown in FIG. 9 involves a variable delay association with each antenna element. Since the contribution of any one element is a small fraction of the total, phasing by varying a single delay within a summation configuration would be an insensitive process. Multiplication shown in FIG. 10 provides the possible alternative of multiple correlation, whereby the element delays might be adjusted, one by one, in a process wherein only the output from the region of interest is coherent. The difficulty exists that the fraction of the thermal energy that is used becomes small as resolution improves in three dimensions.

In FIG. 10, a possible multiple correlation configuration using three multipliers is shown. In the calibration mode, any two of the antenna transmission leads are connected to a common antenna. The output then represents a unique region in three dimensions for any pair of line delays, as a result of trilateration. In the adjust mode, one of the lines to the common antenna is removed and connected through a variable delay to the antenna to be adjusted. The delay is varied until the four-way smoothed product is maximum. The hybrid use of summation and multiplication is a possibility, in which each of the three basic antennas might consist of an array having beam-narrowing and power gain as illustrated in FIG. 11. The antenna beams could be steered adaptively, based on coarse-and-fine measurement logic.

Figure 12:
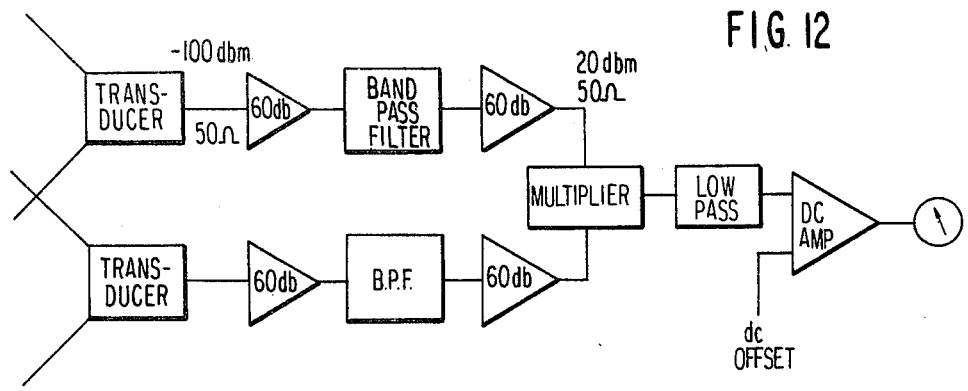
FIG. 12 is a diagram of a feasibility experiment for acoustic thermography.
Figure 13:
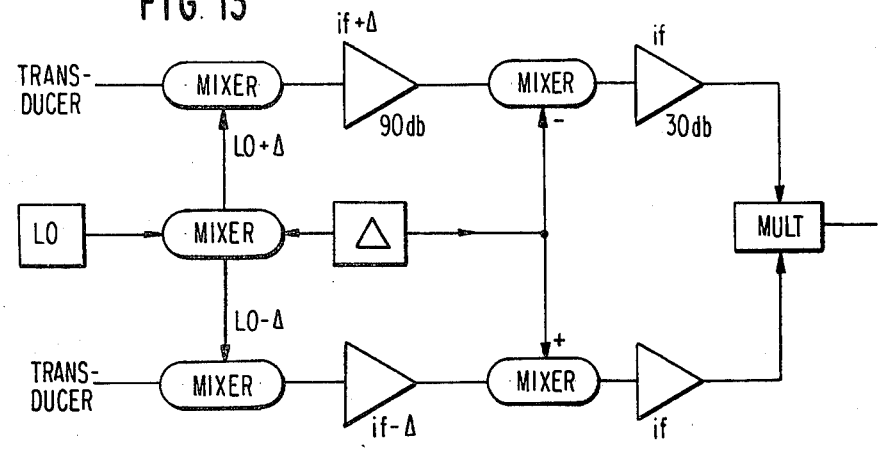
FIG. 13 illustrates a modification of the basic system shown in FIG. 12 which employs superheterodyne up-conversion of the base band signals.

FIG. 12 illustrates a feasibility experiment system diagram for acoustic correlation thermography. Although pre-amplification in this system is in the baseband of the detected thermal energy, the superheterodyne up-conversion shown in FIG. 13 has several advantages.

(1) Correlated pickup can be minimized by using separate IF bands for the two channels.

(2) Spurious frequency products arising from non-linearity effects or limiting can be caused to occur outside the IF bands.

(3) Wide bandwidths can be practically handled as smaller fractions of the band center frequency resulting in simplified filtering and smaller components.

Figure 14:
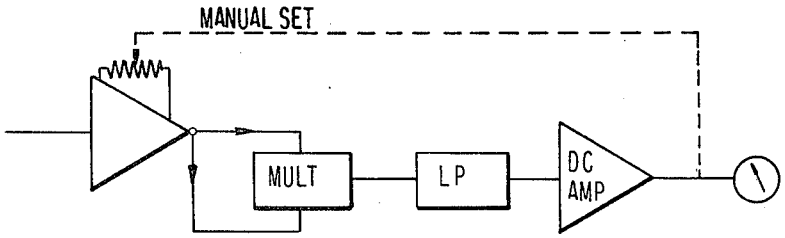
FIG. 14 is a diagram illustrating the method of preamplifier gain adjustment.

In linear implementation, the output level of each of the channels should be below the saturation levels of the amplifier and multiplier if the superposition theorem is to apply, and the thermal information of interest is not to be lost. As a matter of initial adjustment and perhaps intermittently thereafter, both multiplier inputs may be connected to the output of a single channel as shown in FIG. 14. The filtered multiplier output may then be set to a specified d-c level by adjusting the gain in each channel.

Alternatively, certain non-linear implementations could be advantageous. For example, detecting only zero crossings of the signals with a bilateral clipper simplifies the electronics with little loss of accuracy. Also, a sufficient fraction of the information could be handled with reduced equipment dynamic range requirements.

Figure 15:
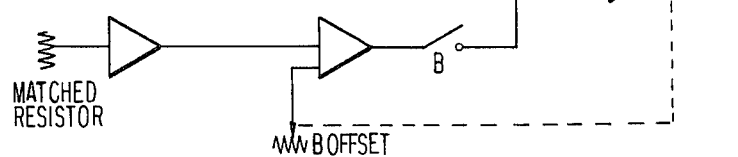
FIG. 15 is a diagram illustrating the method of zero adjust to correct for multiplier input biases.

In correlation thermography, there are reference quantities which can be used as bases for comparison in ways loosely analogous to the employment of an input substitute resistor at a reference temperature in the Dicke radiometer. If two matching resistors at body temperature are substituted for the sensors in the input channels, any multiplier d-c output will represent null error under the approximate operating conditions of the system, and may be used as an offset correction. Or more elaborately, as shown in FIG. 15, if a single matching resistor is substituted in either channel while the transducer is used in the other channel, there should be no d-c output from the multiplier. If output is obtained (which may be different when substitution is effected in the two channels), the d-c offsets may be used separately to correct the two conditions at the multiplier inputs. If the volume from which correlated thermal energy arrives is increased sufficiently by widening the beamwidth and/or broadening the correlation time interval, the indicated temperature should approach a local average body temperature. Any discrepancy (viz. as a result of emissivity or attenuation changes in the body, or changes in receiving system coupling or sensitivity) may be corrected by adjusting the system gain. The differential temperature of any resolvable volume within the increased volume may then be measured with respect to the average value for its surroundings, (or relative to a reference remote volume if desired, as in hyperthermia where the entire local volume may be heated). If the volume from which correlated thermal energy arrives is shifted approximately one resolution element in beam-angle and/or correlation delay time, the differential indication will be a measure of fine-grain thermal gradient along the locus of shift. This type of processing is potentially useful for instance in observing the outlines or interfaces of masses within the body which may have slightly different temperatures.

Since the optimum conditions of search, switching, and reference determination will vary depending on the nature of what is sought and its location, and what is already known about it, the preferred means for processing is a microprocessor with flexible programming rather than any single simplistic hard-wired solution.

In general it will be advantageous to use a-c amplification of the changes in multiplier output level when switching between volume temperatures, but the dwell time in each mode will need to be optimized for each situation (resolving 0.1° in a difference of 1° from local average temperature requires much less linearity, dynamic range, and stability than resolving small differences in a 310° measurement, but the needed measurement times can vary, and in some cases such as scale factor, the entire absolute temperature needs to be measured).

Figure 16:
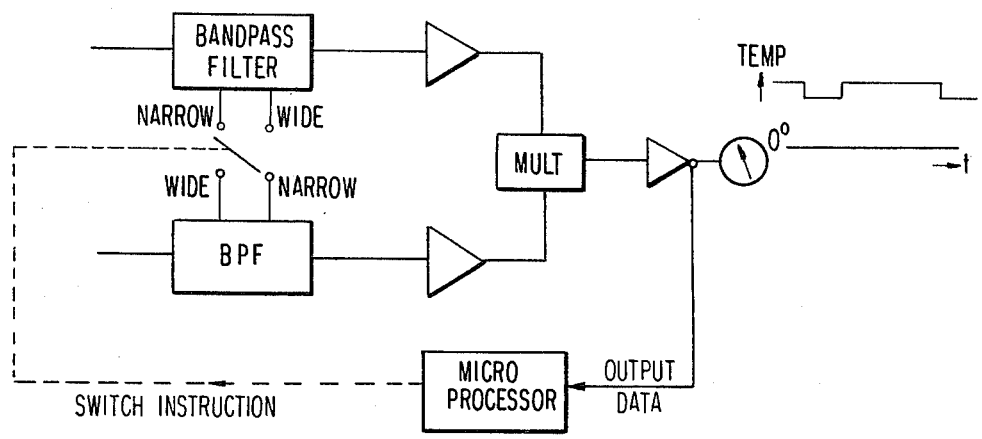
FIG. 16 is a diagram showing narrow band switching to expand correlation volume.
Figure 16:
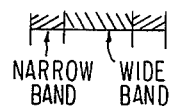
Figure 17:
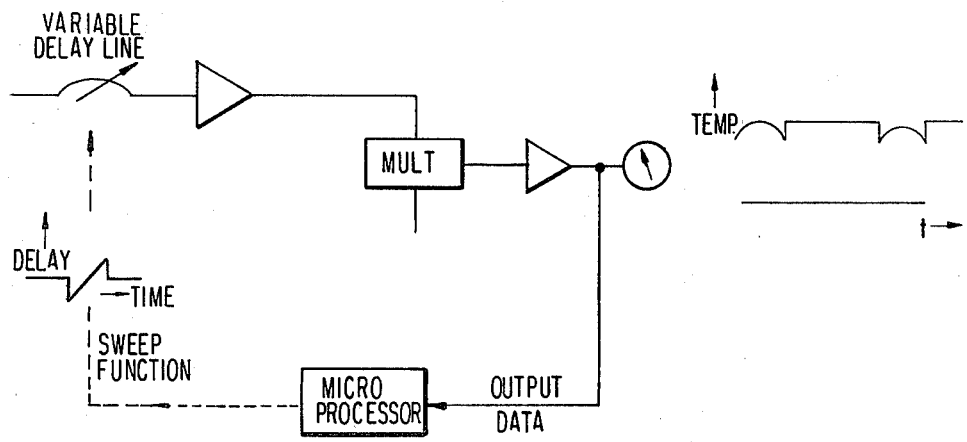
FIG. 17 is a diagram showing delay sweep to expand correlation volume.

The mechanisms for extended volume measurement of temperature could include switching to wider-beam transducers and/or narrowing the bandwidth of the pre-amplifier channel filters and/or inserting varying relative delay elements in one or both of the pre-amplifier channels. FIG. 16 illustrates switching between two bandwidths of the system. The mechanisms for gradient measurement could include mechanical or electronic beam angle shifting and/or switching a differential delay line between channels. For that function alone, the switched states are similar, and square-wave switching might be appropriate. FIG. 17 illustrates a method to continually vary the location of the correlation volume by varying the delay in one of the amplifier channels.

Figure 18:
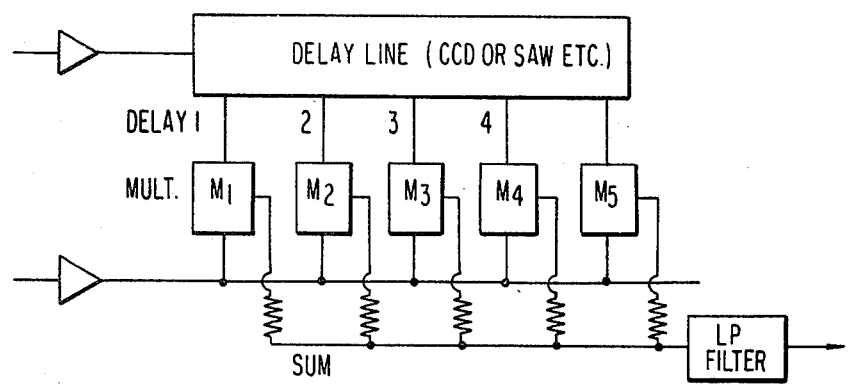
FIGS. 18 and 19 are diagrams of processing networks for the facing geometry shown in FIG. 6.

In the case of the facing geometry shown in FIG. 6, straight forward correlation processing tends either to give a narrow correlated volume if wide bandwidth is used, or degraded averaging if a narrow bandwidth is used. To combine both enhanced effective width of the correlated volume and effective bandwidth, two type of processing may be used. In the first, shown in FIG. 18, direct currents corresponding to a number of zones are extracted from separate correlations with wide bandwidth and summed. The d-c output components add coherently, whereas the noise components are incoherent.

Figure 19:
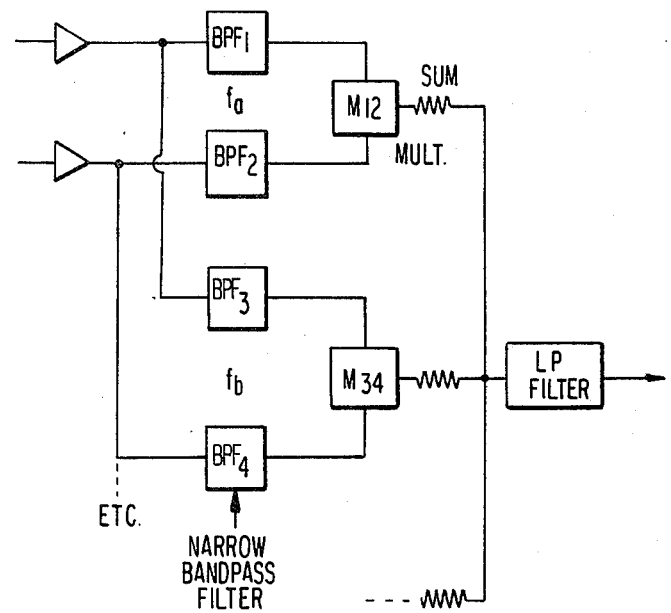
Figure 20:
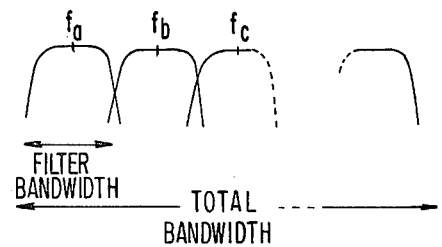
FIG. 20 is a graphical illustration of the channel separation in the processing network of FIG. 19.

In the second type of processing shown in FIG. 19, parallel narrow-bandwidth channels centered at different frequencies (see FIG. 20) are used to give a diversity of correlation outputs which are added. The second method uses channel separation in the frequency domain analogously to time-domain separation in the first method.

Soft tissue has been mentioned in the above discussion because its acoustic characteristics are fairly uniform, and very little acoustic energy is reflected at boundaries between different layers or types of tissue. However, reflections at large acoustic impedance discontinuities due to bone or air can affect the apparent temperature distribution inferred from the noise power correlations. The presence of any such large impedance discontinuities could be detected by utilizing the acoustic transducers in conventional pulse-echo diagnostic ultrasound modes. The temperature profiles also could be displayed by all the techniques employed for conventional diagnostic ultrasound. Superposition of both types of information would aid in compensating for the effects of inhomogeneities and would give more diagnostic information than either display alone.

The diagnostic usefulness of temperature measurements by probe inserted in body cavities is well-known. This invention extends diagnostic temperature measurements to all parts of the body consisting primarily of soft tissue. The invention has therapeutic applications to monitor temperature changes in almost any procedure involving heating or cooling of body tissues. If heat energy is introduced to a small region of the body by focused ultrasound or other means, monitoring the subsequent change of temperature with time by means of this invention would measure the perfusion, another diagnostically useful quantity.

While the invention has been described with specific reference to preferred embodiments, those skilled in the art will understand that these embodiments illustrate the principles of the invention, and the invention is not limited in its practice to these particular embodiments. For example, while piezoelectric transducers were specifically described, other mechanical-vibrations-to-electrical-signal transducers may be used with equal effect. These would include recently developed transducers employing fiber optics and lasers to first convert the mechanical vibrations to an optical signal or modulation which, in turn, is converted to an electrical signal.

Broadly, what the invention provides is a way to non-invasively measure temperature inside the living as well as inanimate bodies by means of detecting thermally-generated noise correlations. By measuring the noise power correlations over a suitable frequency range, the temperature in a well-defined volume can be determined.

We claim:

1. A passive remote thermal radiation sensing and processing system for non-invasive temperature measurement of the interior of a body, said system comprising:
   at least first and second directional receiving means for receiving thermally-generated energy from inside said body and generating corresponding electrical signals, each of said first and second directional receiving means having a defined directional receiving pattern and said first and second directional receiving means being adapted to be coupled with the surface of said body at different locations about said body so that their directional receiving patterns intersect;
   multiplier means connected to receive the electrical signals generated by said first and second directional receiving means for producing a product output signal proportional to the product of said electrical signals; and
   averaging means connected to said multiplier means for averaging said product output signal over a period of time to generate a correlation output signal which is a measure of the thermally-generated energy within the volume of intersection of the directional receiving patterns of said first and second directional receiving means.

2. A passive remote thermal radiation sensing and processing system as recited in claim 1 wherein a plurality of directional receiving means greater than two are coupled with the surface of the body and said multiplier means comprises:
   a plurality of delay means, each of different time delay value and connected to receive the output of a different one of said plurality of directional receiving means, and
   a plurality of multipliers, each connected to receive as inputs the outputs of a different pair of delay means or a pair of multipliers in a tree configuration, the output of the last multiplier in the tree being connected to said averaging means.

3. A passive remote thermal radiation sensing and processing system as recited in claim 1 wherein a plurality of directional receiving means greater than two are coupled with the surface of the body and said multiplier means comprises:
   a plurality of delay means, each of different time delay value and connected to receive the output of a different one of said plurality of directional receiving means, and
   summing means connected to sum the outputs of said plurality of delay means and provide a summed output to said averaging means.

4. A passive remote thermal radiation sensing and processing system as recited in claim 1 further comprising delay means connected between one of said directional receiving means and said multiplier means.

5. A passive remote thermal radiation sensing and processing system as recited in claim 4 wherein said delay means is variable.

6. A passive remote thermal radiation sensing and processing system as recited in claim 7 wherein said antennas are each comprised of an array of antennas.

7. A passive remote thermal radiation sensing and processing system as recited in claim 1 wherein said directional receiving means are directional antennas and said thermally-generated energy is electromagnetic energy.

8. A passive remote thermal radiation sensing and processing system as recited in claim 1 wherein said directional receiving means are acoustic transducers and the thermally-generated energy is acoustical energy.

9. A passive remote thermal radiation sensing and processing system as recited in claim 1 wherein said directional receiving means are positioned so that their directional receiving patterns intersect at an angle $\alpha$ in the range of $0° < \alpha \leq 180°$.

10. A passive remote thermal radiation sensing and processing system as recited in claim 9 wherein said angle is approximately 180° and said multiplier means comprises:
    a delay line having a plurality of taps, said delay line being connected to receive as an input the electrical signal from one of said directional receiving means and providing said electrical signal at each of said taps in predetermined time delayed increments;
    a plurality of multipliers each connected with one input to a corresponding one of said taps and the other input in common to the second one of said directional receiving means; and
    summing means for summing the outputs of said multipliers and providing a summed output signal to said averaging means.

11. A passive remote thermal radiation sensing and processing system as recited in claim 9 wherein said angle is approximately 180° and said multiplier means comprises:

first and second identical pluralities of band pass filters defining contiguous frequency channels, each band pass filter of said first plurality being connected to receive as an input the electrical signal from one of said directional receiving means while each band pass filter of said second plurality being connected to receive as an input the electrical signal from a second one of said transducers;

a plurality of multipliers each of which having its inputs connected to the outputs of corresponding band pass filters of said first and second pluralities; and summing means for summing the outputs of said multipliers, and providing a summed output signal to said averaging means.

12. A passive remote thermal radiation sensing and processing system as recited in claim 1 further comprising display means connected to said averaging means for displaying a representation of said correlation output signal.

13. A passive remote thermal radiation sensing and processing system as recited in claim 2 wherein each of said delay means is variable.

14. A passive remote thermal radiation sensing and processing system as recited in claim 1 wherein the intersection of said directional receiving patterns is an overlap of respective far-field patterns.

15. A passive remote thermal radiation sensing and processing system as recited in claim 1 wherein the intersection of said directional receiving patterns is an overlap of respective near-field patterns.

16. A passive remote thermal radiation sensing and processing system as recited in claim 1 further comprising:

first and second mixing means respectively connected to receive the electrical signals generated by said first and second directional receiving means; and local oscillator means for supplying a local oscillator signal to said first and second mixing means, said first and second mixing means producing intermediate frequency signals which are supplied to said multiplier means.

17. A passive remote thermal radiation sensing and processing means as recited in claim 16 further comprising:

first and second amplifying means respectively connected to amplify the intermediate frequency signals produced by said first and second mixing means;

third and fourth mixing means respectively connected to receive the outputs of said first and second amplifying means;

fifth mixing means connected to receive the local oscillator signal from said local oscillator means; and offset oscillator means for supplying an offset oscillator signal to said third, fourth and fifth mixing means, said third and fourth mixing means producing intermediate frequency signals which are supplied to said multiplier means, said fifth mixing means producing sum and difference local oscillator signals which are supplied to said first and second mixing means.

18. A passive remote thermal radiation sensing and processing system as recited in claim 1 further comprising first and second switchable bandpass filters respectively connected to receive the electrical signals generated by said first and second directional receiving means, said filters being switchable between wide and narrow bandpass characteristics, the outputs of said filters being supplied to said multiplier means.

19. A passive remote thermal radiation sensing and processing system as recited in claim 18 further comprising microprocessor means responsive to the output of said averaging means for switching said first and second switchable bandpass filters between said wide and narrow bandpass characteristics.

20. A passive remote thermal radiation sensing and processing system as recited in claim 5 further comprising microprocessor means responsive to the output of said averaging means for adjusting the delay variation of said delay means.

* * * * *